(12) United States Patent
Metkar et al.

(10) Patent No.: US 10,457,657 B2
(45) Date of Patent: Oct. 29, 2019

(54) PROCESSES FOR PREPARING 2,5-FURANDICARBOXYLIC ACID AND ESTERS THEREOF

(71) Applicants: E I DU PONT DE NEMOURS AND COMPANY, Wilmington, DE (US); ARCHER DANIELS MIDLAND COMPANY, Decatur, IL (US)

(72) Inventors: Pranit S. Metkar, Wilmington, DE (US); Ronnie Ozer, Arden, DE (US); Bhuma Rajagopalan, Wilmington, DE (US)

(73) Assignees: DUPONT INDUSTRIAL BIOSCIENCES USA, LLC, Wilmington, DE (US); ARCHER DANIELS MIDLAND COMPANY, Decatur, IL (US)

(*) Notice: Subject to any disclaimer, the term of this patent is extended or adjusted under 35 U.S.C. 154(b) by 0 days.

(21) Appl. No.: 16/159,891

(22) Filed: Oct. 15, 2018

(65) Prior Publication Data

US 2019/0047973 A1  Feb. 14, 2019

Related U.S. Application Data

(63) Continuation of application No. 15/743,015, filed as application No. PCT/US2016/043296 on Jul. 21, 2016, now abandoned.

(60) Provisional application No. 62/196,808, filed on Jul. 24, 2015.

(51) Int. Cl.
*C07D 307/02* (2006.01)
*C07D 307/68* (2006.01)

(52) U.S. Cl.
CPC ............................ *C07D 307/68* (2013.01)

(58) Field of Classification Search
CPC .......................................... C07D 307/68
USPC ................................................ 549/485
See application file for complete search history.

(56) References Cited

U.S. PATENT DOCUMENTS 8,791,277 B2 * 7/2014 Janka ............... C07D 307/68
549/485

FOREIGN PATENT DOCUMENTS

| WO | 2011/043661 | 4/2011 |
| WO | 2013/033058 | 3/2013 |

OTHER PUBLICATIONS

International Search Report dated Oct. 17, 2016 in PCT/US2016/043296.
Written Opinion dated Oct. 17, 2016 in PCT/US2016/043296.
Extended European Search Report dated Dec. 5, 2018 in European Application No. 18190578.7 (5 pages).

* cited by examiner

*Primary Examiner* — Taylor V Oh
(74) *Attorney, Agent, or Firm* — Grüneberg and Myers PLLC

(57) ABSTRACT

A process for producing furan dicarboxylic acid or an ester thereof from a feedstock comprising hydroxymethyl furfural (HMF) and humins is disclosed. Humins are a byproduct from reactions forming HMF from sugars and are typically removed from the HMF prior to any further processing. A humins-containing HMF feedstock is utilized to produce furan dicarboxylic acids and ester substantially free from humins.

4 Claims, No Drawings

PROCESSES FOR PREPARING 2,5-FURANDICARBOXYLIC ACID AND ESTERS THEREOF

CROSS-REFERENCE TO RELATED APPLICATION

This application is a continuation of U.S. application Ser. No. 15/743,015, filed on Jan. 9, 2018, which is a National Stage entry under § 371 of International Application No. PCT/US2016/043296, filed on Jul. 21, 2016, which itself claims benefit of priority to U.S. Provisional Application No. 62/196,808 filed on Jul. 24, 2015, the contents of which are incorporated by reference.

FIELD OF THE DISCLOSURE

The present disclosure is directed towards processes for preparing 2,5-furandicarboxylic acid and esters thereof, especially diesters thereof, from mixtures comprising 5-hydroxymethyl furfural and humins.

BACKGROUND OF THE DISCLOSURE

Poly (trimethylene furandicarboxylate (PTF) is a renewable polyester and can be synthesized via the polycondensation reaction of 2,5-furandicarboxylic acid or 2,5-furandicarboxylic acid diester with 1,3-propane diol. Compared with polyethylene terephthalate (PET), PTF demonstrates improved oxygen and carbon dioxide barrier properties that are very important for the carbonated beverage and food packaging industry.

The quality of the 2,5-furandicarboxylic acid diester, especially the color of the monomer is important for obtaining the high quality, colorless PTF that is required for the beverage, food and packaging industries. The process for producing 2,5-furandicarboxylic acid and its diesters in a renewable manner proceeds via the oxidation of hydroxymethyl furfural (HMF). HMF from renewable resources is often contaminated with highly colored polymeric impurities called humins. The removal of humins from processes producing furandicarboxylic acid and its diesters continues to be a problem.

The present disclosure relates to efficient processes for producing both furan dicarboxylic acid and its diesters that are substantially free from humins, from hydroxymethyl furfural contaminated with humins.

SUMMARY OF THE DISCLOSURE

The present disclosure relates to a process comprising:
a) oxidizing a feedstock comprising HMF and humins to produce a mixture comprising crude humins-containing FDCA;
b) separating the mixture to obtain a solid FDCA/humins composition;
c) esterifying the solid FDCA/humins composition with an alcohol to produce a crude ester of FDCA; and
d) purifying the crude ester of FDCA obtained in step c) by distillation or by sublimation to produce a purified ester of FDCA substantially free of humins.

In other embodiments, the process comprises:
i) oxidizing a feedstock comprising HMF and humins in a solvent to produce a mixture comprising crude humins-containing FDCA; and
ii) filtering the mixture under high temperature to obtain a filtrate comprising FDCA substantially free of humins, wherein the filtration temperature is sufficiently high to keep the FDCA soluble in the solvent.

In still further embodiments, the process comprises:
i) oxidizing a feedstock comprising HMF and humins in a solvent to produce a mixture comprising crude humins-containing FDCA;
ii) filtering the mixture under high temperature to obtain a filtrate comprising FDCA substantially free of humins, wherein the filtration temperature is sufficiently high to keep the FDCA soluble in the solvent;
iii) esterifying the FDCA substantially free of humins with an alcohol to produce a crude ester of FDCA; and
iv) purifying the crude ester of FDCA obtained in step iii) by distillation or sublimation.

DETAILED DESCRIPTION OF THE DISCLOSURE

The disclosures of all cited patent and non-patent literature are incorporated herein by reference in their entirety.

As used herein, the term "embodiment" or "disclosure" is not meant to be limiting, but applies generally to any of the embodiments defined in the claims or described herein. These terms are used interchangeably herein.

Unless otherwise disclosed, the terms "a" and "an" as used herein are intended to encompass one or more (i.e., at least one) of a referenced feature.

The features and advantages of the present disclosure will be more readily understood by those of ordinary skill in the art from reading the following detailed description. It is to be appreciated that certain features of the disclosure, which are, for clarity, described above and below in the context of separate embodiments, may also be provided in combination in a single element. Conversely, various features of the disclosure that are, for brevity, described in the context of a single embodiment, may also be provided separately or in any sub-combination. In addition, references to the singular may also include the plural (for example, "a" and "an" may refer to one or more) unless the context specifically states otherwise.

The use of numerical values in the various ranges specified in this application, unless expressly indicated otherwise, are stated as approximations as though the minimum and maximum values within the stated ranges were both proceeded by the word "about". In this manner, slight variations above and below the stated ranges can be used to achieve substantially the same results as values within the ranges. Also, the disclosure of these ranges is intended as a continuous range including each and every value between the minimum and maximum values.

As used herein:
The acronym FDCA means 2,5-furan dicarboxylic acid.
The acronym FFCA means 5-formylfuran-2-carboxylic acid.
The acronym FDME means 2,5-furan dicarboxylic acid dimethyl ester.
The acronym FDMME means the monomethyl ester of 2,5-furan dicarboxylic acid.
The acronym FFME means the methyl ester of 5-formylfuran-2-carboxylic acid.
The acronym HMF means 5-hydroxymethyl furfural.
The acronym AcMF means 5-acetoxymethyl-2-furaldehyde.
The term HMF means hydroxymethyl furfural and should also be understood to include derivatives of HMF wherein HMF has reacted with the solvent or with another HMF molecule or derivative to form directly related derivatives of HMF. Examples of HMF derivatives can include ethers when the solvent includes an alcohol and esters when the solvent includes a carboxylic acid.

The term HMF dimer refers to the product of etherification of two molecules of HMF to form 5,5'-oxy(bismethylene)-2-furaldehyde.

The term "humins" means a highly colored, generally brown to black, amorphous or non-crystalline polymers resulting from the dehydration of sugars. Humins are generally insoluble in water.

The phrase "substantially free of humins" means a composition that contains less than 100 parts per million of humins as measured by HPLC or SEC analytical methods. In other embodiments, the composition contains less than 75 ppm of humins, or less than 50 ppm of humins or less than 25 ppm humins or less than 20 ppm humins or less than 15 ppm humins or less than 10 ppm humins, as measured by HPLC/SEC.

The phrase "ester of FDCA" means a composition comprising greater than 50 percent by weight of the diester of 2,5-furandicarboxylic acid, based on the total weight of the ester of FDCA. The remainder of the composition can be the monoester of 2,5-furandicarboxylic acid, the ester of 5-formylfuran-2-carboxylate, 5-formylfuran-2-carboxylic acid, 2,5-furandicarboxylic acid or a combination thereof. In other embodiments, the diester can comprise greater than 90 percent or greater than 95 percent or greater than 96 percent or greater than 97 percent or greater than 98 percent or greater than 99 percent by weight of the ester of FDCA, with the other furan compounds making up the remainder of the composition. Furthermore, the percentage by weight is based on the dry composition, for example, a composition dried for at least 8 hours in a vacuum oven at a temperature in the range of from 40° C. to 100° C. and at a pressure of less than or equal to 0.5 bar.

The phrase "at a temperature sufficiently high to keep the FDCA soluble in the solvent" means a temperature in the range of from 50° C. to 275° C., so that at least 95 percent by weight of the FDCA is dissolved in the solvent, based on the total amount of FDCA in the mixture.

The phrase "alcohol source" means a molecule which, in the presence of water and optionally an acid, forms an alcohol.

In some embodiments, the disclosure relates to a process comprising:
a) oxidizing a feedstock comprising HMF and humins to produce a mixture comprising crude humins-containing FDCA;
b) separating the mixture to obtain a solid FDCA/humins composition;
c) esterifying the solid FDCA/humins composition to produce a crude ester of FDCA; and
d) purifying the crude ester of FDCA obtained in step c) by distillation or by sublimation to produce a purified ester of FDCA substantially free of humins.

In other embodiments, the process comprises:
i) oxidizing a feedstock comprising HMF and humins in a solvent to produce a mixture comprising crude humins-containing FDCA mixture; and
ii) filtering the mixture under high temperature to obtain a filtrate comprising FDCA substantially free from humins, wherein the filtration temperature is sufficiently high to keep the FDCA soluble in the solvent.

In still further embodiments, the process comprises:
i) oxidizing a feedstock comprising HMF and humins in a solvent to produce a mixture comprising crude humins-containing FDCA mixture;
ii) filtering the mixture under high temperature to obtain a filtrate comprising FDCA substantially free from humins, wherein the filtration temperature is sufficiently high to keep the FDCA soluble in the solvent;
iii) esterifying the FDCA substantially free of humins to produce a crude ester of FDCA; and
iv) purifying the crude ester of FDCA obtained in step c) by distillation or sublimation.

The feedstock comprising HMF and humins can be produced by the dehydration of hexose sugars, starch, amylose, galactose, cellulose, hemicellulose, inulin, fructan, glucose, fructose, sucrose, maltose, cellobiose, lactose, and/or sugar oligomers. Depending upon the dehydration process conditions, the feedstock can comprise HMF and humins, optionally further comprising one or more of an HMF ether or an HMF ester, for example, 5-acetoxymethyl-2-furaldehyde. The amount of humins in the feedstock can vary depending upon the process conditions used to form the HMF. In some embodiments, the amount of humins in the feedstock comprising HMF and humins can be in the range of from greater than or equal to 10 parts per million (ppm) to up to 500,000 ppm, based on the total weight of HMF and humins in the feedstock. In other embodiments, the amounts of humins can be in the range of from 100 ppm to 500,000 ppm or from 2500 ppm to 250,000 ppm or from 10,000 to 200,000 ppm or from 50,000 to 200,000 ppm, based on the total weight of HMF and humins.

The oxidation step a) can be conducted by contacting a feedstock comprising 5-hydroxymethyl furfural (HMF) and humins with an oxidant in the presence of an oxidation catalyst to produce a crude humins-containing FDCA. The oxidation step is typically carried out in a solvent, for example, acetic acid or a mixture of acetic acid and water. The oxidation catalyst can be a homogeneous oxidation catalyst.

Any suitable homogeneous oxidation catalyst which is effective for oxidizing HMF, HMF esters, or HMF ethers to FDCA and/or derivatives of FDCA can be used. The homogeneous oxidation catalysts can include, for example, metal catalysts comprising one or more transition metals. In some embodiments, the metal catalyst comprises cobalt, manganese or a combination thereof. In other embodiments, the metal catalyst further comprises zirconium or cerium. The oxidation catalyst may further include bromine. In some embodiments, the metal catalyst may react with the bromine and form in-situ metal bromides. In some embodiments, the metal catalyst comprises or consists essentially of from 59 to 5900 parts per million of Co, from 55 to 5500 parts per million of Mn, and from 203 to 20000 parts per million of Br. All of the parts per million of the catalyst are based on the total weight of the oxidation reaction mixture. Still other metals have previously been found useful for combining with Co/Mn/Br, for example, Zr and/or Ce and may be included.

Each of the metal components can be provided in any of their known ionic forms. Preferably the metal or metals are in a form that is soluble in the oxidation solvent. Examples of suitable counterions for cobalt and manganese include, but are not limited to, carbonate, acetate, acetate tetrahydrate and halide. In some embodiments, the bromine can be in the form of the bromide, for example, hydrogen bromide, sodium bromide, ammonium bromide or potassium bromide. In some embodiments, cobalt acetate, cobalt acetate tetrahydrate, manganese acetate and/or manganese acetate tetrahydrate can be used.

The oxidation step can be performed at a temperature in the range of from 120° C. to 250° C. In other embodiments, the oxidation step can be performed at a temperature in the range of from 125° C. to 250° C. or 130° C. to 240° C. The oxidation step further comprises an oxidant, for example, oxygen gas or an oxygen-containing gas. As an oxygen-containing gas, air or a mixture of oxygen and nitrogen can be used. In some embodiments, the pressure of the oxidant in step a) is such that an oxygen partial pressure of from 0.2 to 100 bar is provided. In other embodiments, the oxygen partial pressure can be in the range of from 0.2 to 50 bar or from 0.2 to 30 bar or from 0.2 to 21 bar.

The oxidation step a) produces a mixture comprising crude humins-containing FDCA. Step b) comprises separating the mixture to obtain a solid FDCA/humins composition. The solid FDCA/humins composition can be separated by filtration or by centrifugation. The separation can be conducted at a temperature at or below the temperature of the oxidation temperature of step a). In some embodiments, the separation step is conducted at a temperature below the oxidation temperature, for example, a temperature in the range of from 20° C. to 200° C. In other embodiments, the separation temperature is in the range of from 30° C. to 175° C. or from 40° C. to 150° C. The oxidation mixture comprising the crude humins-containing FDCA from step a) can be cooled in the oxidation vessel, in a separate vessel or in a series of vessels that gradually cool the reaction temperature to the desired separation temperature. In some embodiments, the crude humins-containing FDCA is cooled via evaporative cooling via a series of evaporative cooling vessels.

Separation of the mixture yields a solid FDCA/humins composition and a mother liquor composition. In some embodiments, the solid FDCA/humins composition comprises in the range of from greater than or equal to 10 ppm to 100,000 ppm of humins, based on the total weight of the FDCA and the humins. In other embodiments, the solids FDCA/humins composition comprises in the range of from 100 ppm to 50,000 ppm, or from 500 ppm to 25,000 ppm, or from 1,000 to 20,000 ppm, or from 10,000 to 20,000 ppm of humins, based on the total weight of FDCA and humins. The solid FDCA/humins composition obtained from the separation step can be used as is, without a further purification step.

In step c), the solid FDCA/humins composition obtained in step b) can be esterified to produce a crude ester of FDCA. The solid FDCA/humins can be used, as is from step b), and can be in the form of a dry solid or a wet cake. The esterification can be accomplished by heating the solids FDCA/humins composition with an excess of an alcohol having the range of from 1 to 12 carbon atoms, especially alkyl alcohols. Suitable alcohols can include, for example methanol, ethanol, propanol, butanol, pentanol, hexanol, heptanol, octanol, nonanol, decanol, undecanol, dodecanol or isomers thereof. In some embodiments, the alcohol is in the range of from 1 to 6 carbon atoms or in the range of from 1 to 4 carbon atoms or in the range of from 1 to 2 carbon atoms. In some embodiments, the alcohol is methanol and the ester of FDCA is FDME.

In some embodiments, the percentage of FDCA and alcohol that can be fed to the reactor can be expressed as a weight percentage of the FDCA based on the total amount of FDCA and the alcohol. For example, the weight of FDCA can be in the range of from 1 to 70 percent by weight, based on the total weight of the FDCA and the alcohol. Correspondingly, the alcohol can be present at a weight percentage of from about 30 to 99 percent by weight, based on the total amount of FDCA and the alcohol. In other embodiments, the FDCA can be present in the range of from 2 to 60 percent, or from 5 to 50 percent, or from 10 to 50 percent, or from 15 to 50 percent, or from 20 to 50 percent by weight, wherein all percentages by weight are based on the total amount of FDCA and the alcohol.

In other embodiments, the ratio of alcohol to the FDCA can be expressed in a molar ratio wherein the molar ratio of the alcohol to the FDCA be in the range of from 2.01:1 to 40:1. In other embodiments, the molar ratio of the alcohol to FDCA can be in the range of from 2.2:1 to 40:1, or 2.5:1 to 40:1, or 3:1 to 40:1, or 4:1 to 40:1, or 8:1 to 40:1, or 10:1 to 40:1, or 15:1 to 40:1, or 20:1 to 40:1, or 25:1 to 40:1, or 30:1 to 40:1.

At least a portion of the alcohol can be replaced with an alcohol source. The alcohol source is a molecule which in the presence of water and optionally an acid forms an alcohol. In some embodiments, the alcohol source is an acetal, an orthoformate, an alkyl carbonate, a trialkyl borate, a cyclic ether comprising 3 or 4 atoms in the ring or a combination thereof. Suitable acetals can include, for example, dialkyl acetals, wherein the alkyl portion of the acetal comprises in the range of from 1 to 12 carbon atoms. In some embodiments, the acetal can be 1,1-dimethoxyethane (acetaldehyde dimethyl acetal), 2,2 dimethoxypropane (acetone dimethyl acetal), 1,1-diethoxyethane (acetaldehyde diethyl acetal) or 2,2 diethoxypropane (acetone diethyl acetal). Suitable orthoformates can be, for example, trialkyl orthoformate wherein the alkyl group comprises in the range of from 1 to 12 carbon atoms. In some embodiments, the orthoester is trimethyl orthoformate or triethyl orthoformate. Suitable alkyl carbonates can be dialkyl carbonates wherein the alkyl portion comprises in the range of from 1 to 12 carbon atoms. In some embodiments, the diallyl carbonate is dimethyl carbonate or diethyl carbonate. Suitable trialkyl borates can be, for example, trialkyl borates wherein the alkyl portion comprises in the range of from 1 to 12 carbon atoms. In some embodiments, the trialkyl borate is trimethyl borate or triethyl borate. A cyclic ether can also be used wherein the cyclic ether has 3 or 4 carbon atoms in the ring. In some embodiments, the cyclic ether is ethylene oxide or oxetane. If used, the alcohol source can be used to replace in the range of from 0.1 percent to 100 percent of the alcohol, based on the total weight of the alcohol in the process.

In further embodiments, combinations of the alcohol and the alcohol source can also be used. In some embodiments, the percentage by weight of the alcohol can be in the range of from 0.001 percent to 99.999 percent by weight, based on the total weight of the alcohol and the alcohol source. In other embodiments, the alcohol can be present at a percentage by weight in the range of from 1 to 99 percent, or from 5 to 95 percent, or from 10 to 90 percent, or from 20 to 80 percent, or from 30 to 70 percent, or from 40 to 60 percent, wherein the percentages by weight are based on the total weight of the alcohol and the alcohol source.

The solid FDCA/humins mixture is fed to a reactor and is contacted with an excess of alcohol, optionally with an esterification catalyst. The esterification reaction can be conducted at elevated temperatures, for example, in the range of from 50° C. to 325° C. and at a pressure in the range of from 1 bar and 140 bar for a sufficient time to produce the desired ester of FDCA. In other embodiments, the temperature can be in the range of from 75° C. to 325° C., or from 100° C. to 325° C., or from 125° C. to 325° C. or from 150° C. to 320° C. or from 160° C. to 315° C. or from 170 to 310° C. In other embodiments, the temperature can be in the range of from 50° C. to 150° C., or from 65° C. to 140° C., or from 75° C. to 130° C. In still further embodiments, the temperature can be in the range of from 250° C. to 325° C. or from 260° C. to 320° C., or from 270° C. to 315° C., or from 275° C. to 310° C., or from 280° C. to 310° C. In some embodiments, the pressure can be in the range of from 5 bar to 130 bar, or from 15 bar to 120 bar, or from 20 bar to 120 bar. In other embodiments, the pressure can be in the range of from 1 bar to 5 bar, or 1 bar to 10 bar, or 1 bar to 20 bar. The pressure and temperature of the step c) are chosen so that contents of the reactor comprise a liquid phase and at least a portion of the contents are in the gas phase.

Step c) can optionally be conducted in the presence of an esterification catalyst, for example, the catalyst can be cobalt (II) acetate, iron (II) chloride, iron (III) chloride, iron (II) sulfate, iron (III) sulfate, iron (II) nitrate, iron (III) nitrate, iron (II) oxide, iron (III) oxide, iron (II) sulfide, iron (III) sulfide, iron (II) acetate, iron (III) acetate, magnesium (II) acetate, magnesium (II) hydroxide, manganese (II) acetate, phosphoric acid, sulfuric acid, zinc (II) acetate, zinc stearate, a solid acid catalyst, a zeolite solid catalyst, or a combination thereof. The metal acetates, chlorides and hydroxides can be used as the hydrated salts. In some embodiments, the catalyst can be cobalt (II) acetate, iron (II) chloride, iron (III) chloride, magnesium (II) acetate, magnesium hydroxide, zinc (II) acetate, or a hydrate thereof. In still further embodiments, the catalyst can be iron (II) chloride, iron (III) chloride, or a combination thereof. In other embodiments, the catalyst can be cobalt acetate. In some embodiments, the catalyst can be sulfuric acid, hydrobromic acid, hydrochloric acid, boric acid, or another suitable Brønsted acid. Combinations of any of the above catalysts may also be useful. If present, a catalyst can be used at a rate of 0.01 to 5.0 percent by weight, based on the total weight of the FDCA, alcohol and optionally the alcohol source, and the catalyst. In other embodiments, the amount of catalyst present can be in the range of from 0.2 to 4.0, or from 0.5 to 3.0, or from 0.75 to 2.0, or from 1.0 to 1.5 percent by weight, wherein the percentages by weight are based on the total amount of FDCA, methanol and the catalyst.

The catalyst can also be a solid acid catalyst having the thermal stability required to survive reaction conditions. The solid acid catalyst may be supported on at least one catalyst support. Examples of suitable solid acids include without limitation the following categories: 1) heterogeneous heteropolyacids (HPAs) and their salts, 2) natural or synthetic minerals (including both clays and zeolites), such as those containing alumina and/or silica, 3) cation exchange resins, 4) metal oxides, 5) mixed metal oxides, 6) metal salts such as metal sulfides, metal sulfates, metal sulfonates, metal nitrates, metal phosphates, metal phosphonates, metal molybdates, metal tungstates, metal borates or combinations thereof. The metal components of categories 4 to 6 may be selected from elements from Groups 1 through 12 of the Periodic Table of the Elements, as well as aluminum, chromium, tin, titanium, and zirconium. Examples include, without limitation, sulfated zirconia and sulfated titania.

Suitable HPAs include compounds of the general formula $X_aM_bO_c^{q-}$, where X is a heteroatom such as phosphorus, silicon, boron, aluminum, germanium, titanium, zirconium, cerium, cobalt or chromium, M is at least one transition metal such as tungsten, molybdenum, niobium, vanadium, or tantalum, and q, a, b, and c are individually selected whole numbers or fractions thereof. Nonlimiting examples of salts of HPAs include, for example, lithium, sodium, potassium, cesium, magnesium, barium, copper, gold and gallium, and ammonium salts. Examples of HPAs suitable for the disclosed process include, but are not limited to, tungstosilicic acid $(H_4[SiW_{12}O_{40}].xH_2O)$, tungstophosphoric acid $(H_3[PW_{12}O_{40}].xH_2O)$, molybdophosphoric acid $(H_3[PMo_{12}O_{40}].xH_2O)$, molybdosilicic acid $(H_4[SiMo_{12}O_{40}].xH_2O)$, vanadotungstosilicic acid $(H_{4+n}[SiV_nW_{12-n}O_{40}].xH_2O)$, vanadotungstophosphoric acid $(H_{3+n}[PV_nW_{12-n}O_{40}].xH_2O)$, vanadomolybdophosphoric acid $(H_{3+n}[PV_nMo_{12-n}O_{40}].xH_2O)$, vanadomolybdosilicic acid $(H_{4+n}[SiV_nMo_{12-n}O_{40}].xH_2O)$, molybdotungstosilicic acid $(H_4[SiMo_nW_{12-n}O_{40}].xH_2O)$, molybdotungstophosphoric acid $(H_3[PMo_nW_{12-n}O_{40}].xH_2O)$, wherein n in the formulas is an integer from 1 to 11 and x is an integer of 1 or more.

Natural clay minerals are well known in the art and include, without limitation, kaolinite, bentonite, attapulgite, and montmorillonite.

In an embodiment, the solid acid catalyst is a cation exchange resin that is a sulfonic acid functionalized polymer. Suitable cation exchange resins include, but are not limited to the following: styrene divinylbenzene copolymer-based strong cation exchange resins such as AMBERLYST™ and DOWEX® available from Dow Chemicals (Midland, Mich.) (for example, DOWEX® Monosphere M-31, AMBERLYST™ 15, AMBERLITE™ 120); CG resins available from Resintech, Inc. (West Berlin, N.J.); Lewatit resins such as MONOPLUS™ S 100H available from Sybron Chemicals Inc. (Birmingham, N.J.); fluorinated sulfonic acid polymers (these acids are partially or totally fluorinated hydrocarbon polymers containing pendant sulfonic acid groups, which may be partially or totally converted to the salt form) such as NAFION® perfluorinated sulfonic acid polymer, NAFION® Super Acid Catalyst (a bead-form strongly acidic resin which is a copolymer of tetrafluoroethylene and perfluoro-3,5-dioxa-4-methyl-7-octene sulfonyl fluoride, converted to either the proton ($H^+$), or the metal salt form) available from DuPont Company (Wilmington, Del.).

In an embodiment, the solid acid catalyst is a supported acid catalyst. The support for the solid acid catalyst can be any solid substance that is inert under the reaction conditions including, but not limited to, oxides such as silica, alumina, titania, sulfated titania, and compounds thereof and combinations thereof; barium sulfate; calcium carbonate; zirconia; carbons, particularly acid washed carbon; and combinations thereof. Acid washed carbon is a carbon that has been washed with an acid, such as nitric acid, sulfuric acid or acetic acid, to remove impurities. The support can be in the form of powder, granules, pellets, or the like. The supported acid catalyst can be prepared by depositing the acid catalyst on the support by any number of methods well known to those skilled in the art of catalysis, such as spraying, soaking or physical mixing, followed by drying, calcination, and if necessary, activation through methods such as reduction or oxidation. The loading of the at least one acid catalyst on the at least one support is in the range of 0.1-20 weight percent based on the combined weights of the at least one acid catalyst and the at least one support. Certain acid catalysts perform better at low loadings such as 0.1-5%, whereas other acid catalysts are more likely to be useful at higher loadings such as 10-20%. In an embodiment, the acid catalyst is an unsupported catalyst having 100% acid catalyst with no support such as, pure zeolites and acidic ion exchange resins.

Examples of supported solid acid catalysts include, but are not limited to, phosphoric acid on silica, NAFION®, a sulfonated perfluorinated polymer, HPAs on silica, sulfated zirconia, and sulfated titania. In the case of NAFION® on silica, a loading of 12.5% is typical of commercial examples.

In another embodiment, the solid acid catalyst comprises a sulfonated divinylbenzene/styrene copolymer, such as AMBERLYST™ 70.

In one embodiment, the solid acid catalyst comprises a sulfonated perfluorinated polymer, such as NAFION® supported on silica ($SiO_2$).

In one embodiment, the solid acid catalyst comprises natural or synthetic minerals (including both clays and zeolites), such as those containing alumina and/or silica.

Zeolites suitable for use herein can be generally represented by the following formula $M_{2/n}O.Al_2O_3.xSiO_2.yH_2O$ wherein M is a cation of valence n, x is greater than or equal to about 2, and y is a number determined by the porosity and the hydration state of the zeolite, generally from about 2 to about 8. In naturally occurring zeolites, M is principally represented by Na, Ca, K, Mg and Ba in proportions usually reflecting their approximate geochemical abundance. The cations M are loosely bound to the structure and can frequently be completely or partially replaced with other cations by conventional ion exchange.

The zeolite framework structure has corner-linked tetrahedra with Al or Si atoms at centers of the tetrahedra and oxygen atoms at the corners. Such tetrahedra are combined in a well-defined repeating structure comprising various combinations of 4-, 6-, 8-, 10-, and 12-membered rings. The resulting framework structure is a pore network of regular channels and cages that is useful for separation. Pore dimensions are determined by the geometry of the aluminosilicate tetrahedra forming the zeolite channels or cages, with nominal openings of about 0.26 nm for 6-member rings, about 0.40 nm for 8-member rings, about 0.55 nm for 10-member rings, and about 0.74 nm for 12-member rings (these numbers assume the ionic radii for oxygen). Zeolites with the largest pores, being 8-member rings, 10-member rings, and 12-member rings, are frequently considered small, medium and large pore zeolites, respectively.

In a zeolite, the term "silicon to aluminum ratio" or, equivalently, "Si/Al ratio" means the ratio of silicon atoms to aluminum atoms. Pore dimensions are critical to the performance of these materials in catalytic and separation applications, since this characteristic determines whether molecules of certain size can enter and exit the zeolite framework.

In practice, it has been observed that very slight decreases in ring dimensions can effectively hinder or block movement of particular molecular species through the zeolite structure. The effective pore dimensions that control access to the interior of the zeolites are determined not only by the geometric dimensions of the tetrahedra forming the pore opening, but also by the presence or absence of ions in or near the pore. For example, in the case of zeolite type A, access can be restricted by monovalent ions, such as $Na^+$ or $K^+$, which are situated in or near 8-member ring openings as well as 6-member ring openings. Access can be enhanced by divalent ions, such as $Ca^{2+}$, which are situated only in or near 6-member ring openings. Thus, the potassium and sodium salts of zeolite A exhibit effective pore openings of about 0.3 nm and about 0.4 nm respectively, whereas the calcium salt of zeolite A has an effective pore opening of about 0.5 nm.

The presence or absence of ions in or near the pores, channels and/or cages can also significantly modify the accessible pore volume of the zeolite for sorbing materials. Representative examples of zeolites are (i) small pore zeolites such as NaA (LTA), CaA (LTA), Erionite (ERI), Rho (RHO), ZK-5 (KFI) and chabazite (CHA); (ii) medium pore zeolites such as ZSM-5 (MFI), ZSM-11 (MEL), ZSM-22 (TON), and ZSM-48 (*MRE); and (iii) large pore zeolites such as zeolite beta (BEA), faujasite (FAU), mordenite (MOR), zeolite L (LTL), NaX (FAU), NaY (FAU), DA-Y (FAU) and CaY (FAU). The letters in parentheses give the framework structure type of the zeolite.

Zeolites suitable for use herein include medium or large pore, acidic, hydrophobic zeolites, including without limitation ZSM-5, faujasites, beta, mordenite zeolites or mixtures thereof, having a high silicon to aluminum ratio, such as in the range of 5:1 to 400:1 or 5:1 to 200:1. Medium pore zeolites have a framework structure consisting of 10-membered rings with a pore size of about 0.5-0.6 nm. Large pore zeolites have a framework structure consisting of 12-membered rings with a pore size of about 0.65 to about 0.75 nm. Hydrophobic zeolites generally have Si/Al ratios greater than or equal to about 5, and the hydrophobicity generally increases with increasing Si/Al ratios. Other suitable zeolites include without limitation acidic large pore zeolites such as H-Y with Si/Al in the range of about 2.25 to 5.

The esterification step can produce a crude ester of FDCA comprising the desired diester of FDCA and optionally, further comprising the mono ester of FDCA, the alkyl ester of 5-formylfuran-2-carboxylic acid, 5-formylfuran-2-carboxylic acid, and unreacted FDCA. In some embodiments, the product of the esterification can be removed from the reactor by removing a vapor component, wherein the vapor component comprises water, the alcohol and the crude ester of FDCA. If the crude ester of FDCA is removed via the vapor phase, humins remain in the liquid phase and the crude ester of FDCA comprises very little if any humins. Other impurities may be present, but humins generally are not contained in the vapor phase. In other embodiments, the contents of the esterification reactor can be cooled and the crude ester of FDCA can be removed via a solid liquid separation step. The cooling step, if present, can be performed in the esterification reactor, in a separate cooling vessel or in a series of separate cooling vessels, wherein each successive vessel further cools the mixture when compared to the previous cooling vessel. The cooling of the contents of the esterification step c) can cause the ester of FDCA to crystallize. If the crude ester of FDCA is crystallized, then humins will be present in the solids phase. The crude ester of FDCA can then be separated by filtration or centrifugation. Separation of the solids comprising the crude ester of FDCA also yields a mother liquor. The mother liquor can comprise the alcohol and water. If an alcohol source is used, then the mother liquor can also comprise one or more of the by-products from the hydrolysis of the alcohol source. For example, in the presence of water, trimethyl orthoformate is known to form methanol and methyl formate. Other hydrolysis products of the disclosed alcohol sources are well-known in the art and can be present in the mother liquor.

The process further comprises a step d), purifying the crude ester of FDCA obtained in step c) by crystallization, distillation or sublimation to produce a purified ester of FDCA substantially free of humins. In some embodiments, the purification step d) is a distillation step, wherein the distillation is performed at low pressure, for example, in the range of from less than 1 bar to 0.0001 bar. In other embodiments, the pressure can be in the range of from 0.75 bar to 0.001 bar or from 0.5 bar to 0.01 bar. In other embodiments, the purification step d) is a sublimation step wherein the solid crude ester of FDCA is sublimed to provide the purified ester of FDCA substantially free of humins.

In some embodiments, the amount of humins in the purified ester of FDCA is less than 100 ppm as determined by size exclusion chromatography. In still further embodiments, the purified ester of FDCA has a b* color value of less than 3, or less than 2, as determined by LAB color measurement. In other embodiments, the purified ester of FDCA comprises greater than or equal to 99% by weight of the ester of FDCA, wherein the percentage by weight is based on the total amount of a sample of the dried ester of FDCA.

In other embodiments, the disclosure relates to a process comprises:
i) oxidizing a feedstock comprising HMF and humins in a solvent to produce a mixture comprising crude humins-containing FDCA; and
ii) filtering the mixture under high temperature to obtain a filtrate comprising FDCA substantially free of humins, wherein the filtration temperature is sufficiently high to keep the FDCA soluble in the solvent.

The oxidation step can be conducted under the same oxidation conditions as was given above for step a), with the exception that, in some embodiments, the concentration of the FDCA in the solvent is in the range of from 0.1 percent to 15 percent by weight, based on the total weight of the solvent. In other embodiments, the concentration of the FDCA can be in the range of from 0.1 to 12.0 percent by weight. In some embodiments, the solvent for step i) is acetic acid, or mixture of acetic acid and water.

Following the oxidation step, the process further comprises a step ii), filtering the mixture under high temperature to obtain a filtrate comprising FDCA substantially free of humins, wherein the filtration temperature is sufficiently high to keep the FDCA soluble in the solvent. Temperatures sufficiently high to keep the FDCA soluble in the solvent are dependent on the concentration of the FDCA in the solvent, and can easily be determined. For example, in a solvent containing 93 wt. % acetic acid and 7 wt. % water, FDCA is typically soluble up to about 10 percent by weight at a temperature of between 180° C. and 275° C. At lower temperature, for example, temperatures as low as 50° C., lesser amounts of FDCA are soluble in acetic acid or a mixture of acetic acid and water. In some embodiments, the high temperature of the filtration step ii) can be in the range of from 50° C. to 275° C. In other embodiments, the filtration step ii) can be conducted at a temperature in the range of from 75° C. to 250° C. or from 100° C. to 225° C. or from 120° C. to 200° C. It has been found that the solubility of the humins is dependent at least on the solvent composition, for example, the amount of water in the acetic acid. Therefore, the filtration step ii) can provide a filtrate wherein the filtrate comprises FDCA substantially free from humins.

In some embodiments, the filtrate composing FDCA substantially free of humins can be evaporated or distilled to provide solid impure FDCA substantially free of humins. The FDCA substantially free of humins can be purified by any of the known methods, for example, using at least one crystallization step. Suitable crystallization solvents can include for example, acetic acid, a mixture of acetic acid and water or water.

In still further embodiments, the disclosure relates to a process comprising:
i) oxidizing a feedstock comprising HMF and humins in a solvent to produce a mixture comprising crude humins-containing FDCA, wherein the concentration of the FDCA in the solvent is in the range of from 0.1 percent to 15 percent by weight, based on the total weight of the solvent;
ii) filtering the mixture under high temperature to obtain a filtrate comprising FDCA substantially free of humins, wherein the filtration temperature is sufficiently high to keep the FDCA soluble in the solvent;
iii) esterifying the FDCA substantially free of humins to produce a crude ester of FDCA; and
iv) purifying the crude ester of FDCA obtained in step c).

Process steps i) and ii) are identical to steps i) and ii) described above. The process further provides steps iii) and iv). The step iii) of esterifying the FDCA substantially free of humins can be further comprises a step of removing at least a portion of the solvent to provide solid FDCA substantially free of humins. The esterification step iii) can utilize dry solids or a wet cake of the FDCA substantially free of humins. The esterifying step can use the same conditions as described above for the esterification step c). The product of step iii) is a crude ester of FDCA. In some embodiments, the ester of FDCA is a methyl ester of FDCA.

The crude ester of FDCA can be purified in step iv) by crystallization, distillation or sublimation. The process steps for the sublimation are identical to those given for the purification step d).

The described processes can provide a purified ester of FDCA substantially free of humins or FDCA substantially free of humins. The purified ester of FDCA comprises less than 100 ppm humins, a b* value of less than 3 and greater than 99 percent by weight of the diester of FDCA, based on the total weight of the purified ester of FDCA.

Non-limiting examples of the processes disclosed herein include:
1. A process comprising:
   a) oxidizing a feedstock comprising HMF and humins to produce a mixture comprising crude humins-containing FDCA;
   b) separating the mixture to obtain a solid FDCA/humins composition;
   c) esterifying the solid FDCA/humins composition with an alcohol to produce a crude ester of FDCA; and
   d) purifying the crude ester of FDCA obtained in step c) to produce a purified ester of FDCA substantially free of humins.
2. The process of embodiment 1 wherein the purified ester of FDCA is 2,5-furan dicarboxylic acid dimethyl ester.
3. A process comprising:
   i) oxidizing a feedstock comprising HMF and humins in a solvent to produce a mixture comprising crude humins-containing FDCA; and
   ii) filtering the mixture under high temperature to obtain a filtrate comprising FDCA substantially free of humins, wherein the filtration temperature is sufficiently high to keep the FDCA soluble in the solvent.
4. The process of embodiment 3 wherein the high temperature of the filtration step ii) is in the range of from 50° C. to 275° C.
5. The process of embodiment 3, further comprising a step iii) crystallizing the 2,5-furan dicarboxylic acid substantially free of humins to obtain further purified 2,5-furan dicarboxylic acid.
6. The process of embodiment 3 wherein the solvent acetic acid or a mixture of acetic acid and water.
7. A process comprising:
   i) oxidizing a feedstock comprising HMF and humins in a solvent to produce a mixture comprising crude humins-containing FDCA;

ii) filtering the mixture under high temperature to obtain a filtrate comprising FDCA substantially free of humins, wherein the filtration temperature is sufficiently high to keep the FDCA soluble in the solvent;
iii) esterifying the FDCA substantially free of humins with an alcohol to produce a crude ester of FDCA; and
iv) purifying the crude ester of FDCA obtained in step iii) by distillation or sublimation to obtain a purified ester.

8. The process of embodiment 7 wherein the ester of FDCA is a methyl ester of FDCA.

9. The process of embodiment 7 wherein the high temperature of the filtration step ii) is in the range of from 50° C. to 275° C.

10. The process of embodiment 7 wherein the solvent is acetic acid or acetic acid and water.

11. The process of any one of embodiments 1, 3 or 7 wherein the purified ester of FDCA comprises less than 100 ppm humins as determined by size exclusion chromatography, a b* value of less than 3 as determined by LAB color measurement, and greater than 99 percent by weight of the diester of FDCA, based on the total weight of the purified ester of FDCA.

12. The process of any one of embodiments 1 or 7, wherein at least a portion of the alcohol is replaced with an alcohol source.

EXAMPLES

Unless otherwise noted, all chemicals and reagents are available from the Sigma-Aldrich Company, St. Louis, Mo.

ACS grade glacial acetic acid was obtained from Fisher Scientific.

The HMF feed was provided by Archer Daniels Midland (ADM) Company, Decatur, Ill.

Methanol was obtained from EMD Millipore (catalog #MX-04724-6).

Acetonitrile was obtained from Fisher Scientific (catalog #A955-1).

Isopropanol was also obtained from Fisher Scientific (catalog #A4641L1).

The following abbreviations are used in the examples: "° C." means degrees Celsius; "wt %" means weight percent; "g" means gram; "min" means minute(s); "µL" means microliter; "ppm" means microgram per gram, "µm" means micrometer; "mL" means milliliter; "mm" means millimeter and "mL/min" means milliliter per minute; "slpm" means standard liters per minute; "HMF" means 5-(hydroxymethyl)furfural, "AcMF" means 5-(acetoxymethyl)furfural, "DMF" means dimethylformamide, "FFCA" means 5-formyl-2-furancarboxylic acid, "FDCA" means 2,5-furandicarboxylic acid, "FDME" means dimethyl-furan-2,5-dicarboxylate, "FFME" means formyl furan methyl ester, "FDMME" means furan dicarboxylic acid mono methyl ester.

TEST/GENERAL METHODS

HPLC Analysis

HPLC analysis was used as one means to measure the FDCA, FDMME & FDME contents of the product mixture. An Agilent 1200 series HPLC equipped with a ZORBAX™ SB-Aq column (4.6 mm×250 mm, 5 µm) and photodiode array detector was used for the analysis of the reaction samples. The wavelength used to monitor the reaction was 280 nm. The HPLC separation of FDME, FDCA and FDMME was achieved using a gradient method with a 1.0 mL/min flow rate combining two mobile phases: Mobile Phase A: 0.5% v/v trifluoroacetic acid (TFA) in water and Mobile Phase B: acetonitrile. The column was held at 60° C. and 2 µL injections of samples were performed. Analyzed samples were diluted to <0.1 wt % for components of interest in a 50:50 (v/v) acetonitrile/isopropanol solvent. The solvent composition and flow rates used for the gradient method is given in Table 1 with linear changes occurring over the corresponding step whenever the composition changes.

Table 1: Gradient Program for HPLC

TABLE 1

| Step | Start time (min) | Volume % Mobile Phase B, at Beginning of Step | Volume % Mobile Phase B, at End of Step |
|---|---|---|---|
| 1 | 0.0 | 0 | 0 |
| 2 | 6.0 | 0 | 80 |
| 3 | 20.0 | 80 | 80 |
| 4 | 25.0 | 80 | 0 |
| 5 | 25.1 | 0 | 0 |
| 6 | 30.0 | 0 | 0 |

Retention times were obtained by injecting analytical standards of each component onto the HPLC. The amount of the analyte in weight percent was typically determined by injection of two or more injections from a given prepared solution and averaging the area measured for the component using the OpenLAB CDS C.01.05 software. The solution analyzed by HPLC was generated by dilution of a measured mass of the reaction sample with a quantified mass of 50:50 (v/v) acetonitrile/isopropanol solvent. Quantification as performed by comparing the areas determined in the OpenLAB software to a linear external calibration curve at five or more starting material concentrations. Typical $R^2$ values for the fit of such linear calibration curves was in excess of 0.9997.

While the presented HPLC method was used for this analysis, it should be understood that any HPLC method that can discriminate between products, starting materials, intermediates, impurities, and solvent can be used for this analysis. It should also be understood that while HPLC was used as a method of analysis in this work, other techniques such as gas chromatography could also be optionally used for quantification when employing appropriate derivatization and calibration as necessary.

LAB Color Measurements

A Hunterlab COLORQUEST™ Spectrocolorimeter (Reston, Va.) was used to measure the color. Color numbers are measured as APHA values (Platinum-Cobalt System) according to ASTM D-1209. The "b*" color of FDCA and/or FDME solids was calculated from the UV/VIS spectra and computed by the instrument. Color is commonly expressed in terms of Hunter numbers which correspond to the lightness or darkness ("L") of a sample, the color value ("a*") on a red-green scale, and the color value ("b*") on a yellow-blue scale. Each sample was prepared by adding 6 wt. % solids in dimethylformamide (Sigma Aldrich).

Size Exclusion Chromatography (SEC) Method for Humins Analysis

A screening assay to estimate weight concentration of soluble humin byproduct was developed using Size Exclusion Chromatography (SEC). An Alliance 2895 chromatograph (Waters Corporation, Milford, Mass.) was coupled to a 2498 dual-channel UV/Visible detector (Waters Corporation). UV absorbance was collected at wavelengths of 280 and 450 nm. The stationary phase consisting of a 4 column set (SHODEX™ KD-801, KD-802, and two KD-806M) was kept at a constant temperature of 50° C. Dimethylacetamide (Thermo Fisher, Wilmington, Del.) with 0.5% (w/v) lithium chloride (Sigma Aldrich) was used as mobile phase at a flow rate of 1 mL/min. Samples were prepared by dissolving or diluting in mobile phase, followed by agitation at room temperature for 4 hours, filtering using 0.45 μm PTFE (Pall, Fort Washington, N.Y.), and finally injecting 100 μL. A calibration curve was constructed using humin byproduct isolated from an acid-catalyzed fructose dehydration reaction. Resulting humin concentration in research samples was determined by integrating any eluting peak (450 nm absorbance) in the humin region of the chromatogram and comparing peak area to the calibration curve. A lower limit of detection in the sample as prepared was found to be approximately 50 ng humins.

Example 1

Purification of FDCA

Step 1.1 Oxidation of a Feedstock Comprising HMF and Humins

Oxidation of HMF to FDCA was carried out in a 1 L titanium reactor (Autoclave Engineers, Serial #85-00534-1). The reactor was charged with 440 mL of acetic acid, 23 mL of water, 4.566 g of cobalt(II) acetate tetrahydrate, 0.285 g of manganese(II) acetate tetrahydrate, and 632 μL of hydrobromic acid (48%). The reactor was pressurized to 450 psig under an air atmosphere, and heated to a temperature of 200° C. Air was then sparged in through a dip tube which had eight 229 μm diameter holes at a rate of 2.0 slpm when reactor temperature reached 190° C. Nitrogen was fed to the inlet of the condenser at 4.5 slpm. When desired temperature was achieved, the HMF feed was pumped into the reactor at a rate of 0.9 mL/min through another dip tube which was positioned close to the reactor impeller. The composition of the HMF feed was 9.86 wt. % HMF, 19.0 wt. % AcMF, 0.22 wt. % HMF dimer and 8.36 wt. % humins. This addition was performed over a 45 min period. When the addition was complete, the reaction was further heated for an additional 50 min of post oxidation when only air was fed to the reactor. After post oxidation, the reactor was cooled down to room temperature and depressurized. The FDCA solids were then vacuum filtered and dried in a vacuum oven at 75° C. at a pressure of 200-300 torr. After drying, 8.8 g of crude FDCA (with a molar FDCA yield of 59.18%) solids was obtained. A detailed analysis of this sample is given in Table 2. This crude FDCA sample is referred as sample 1.1.

Step 1.2: Esterification of FDCA Containing Humins to FDME

FDCA sample 1.1 was esterified in a 75 mL mini Parr reactor model 5050 equipped with an IKA RCT Basic hotplate stirrer. A total of 6 g of FDCA (sample 1.1), 24 g methanol and TFE stir bar were added to the reactor. The reactor was placed in an aluminum block and was kept insulated. The reactor was then purged a minimum of 5 times with nitrogen. At room temperature, 300 psi of $N_2$ was introduced in the reactor head. The reactor was then heated to a temperature of 200° C. and both the temperature and pressure were monitored. After 4 hr, heat was turned off and the reactor was allowed to cool to room temperature. The pressure was then released and the reactor was opened. The reactor contents (containing mainly FDME product) were removed and transferred to an aluminum pan. Solids were dried overnight on aluminum pan (while methanol was evaporated). The dried solids were then analyzed using HPLC and SEC. This sample of the crude methyl ester of FDCA was referred as Sample 1.2 in Table 2.

Step 1.3: Purification of the Crude Methyl Ester of FDAC via Distillation/Sublimation The solid product obtained after the esterification reaction was purified using sublimation. The sublimation device was a two piece glass unit that was connected together by a metal clamp. The bottom piece of the sublimator had a rounded bottom so that there was a larger area for heat transfer from a heating mantle. The top piece was placed on top of the bottom piece with an o-ring in between so that a seal between the top and bottom was created. The top piece of the device had a conical water jacket that was used to cool the sublimated vapor phase, and allow the solids to collect on the inside of the cone. The top of the conical piece had a glass valve which allowed the device to be connected to a vacuum source. Sublimation conditions were maintained at a pressure of from 15 to 30 torr and a temperature of about 100° C. After completion of the sublimation, the apparatus was disassembled and the sublimation product was collected from the inside of the cone on the top piece. The sublimation bottoms were collected off of the rounded bottom of the bottom piece. The solids collected from top of the sublimator were analyzed for their purity using HPLC, SEC and colorimetry. This sample was referred as Sample 1.3-1 in Table 2. The sublimator was operated in such a way that about 10% of the starting material was purified and collected on top. The rest 90% remained in the bottom. The bottom sample was labeled as Sample 1.3.2.

Results

Table 2: Results Obtained After the Analysis of Solids Collected at the End of Stability Tests

TABLE 2

| Sample | L* | b* | Wt. % FDME | Wt. % FDMME | Wt. % FDCA | Humins (ppm) |
|---|---|---|---|---|---|---|
| 1.1 (after oxidation) | 96.72 | 13.66 | 0.00 | 0.00 | 96.84 | 1403 |
| 1.2 (after esterification | 48.98 | 80.66 | 88.79 | 12.84 | 0.356 | 1045 |
| 1.3-1 (after sublimation, collected from top) | 99.99 | 0.19 | 99.248 | 0.752 | 0 | <10 |
| 1.3-2 (after sublimation, collected from bottom) | 42.46 | 72.65 | 85.273 | 14.389 | 0.338 | 1200 |

From the results shown in Table 2, it has been surprisingly found that humins-containing FDCA can be converted into FDME which can be further purified via sublimation. The FDME obtained at the end of the sublimation did not contain any humins and also had L*>99 and b*<1. This high purity monomer can be used in the manufacture of different polymers. Thus, the above example shows that crude humins-containing FDCA can be purified using esterification followed by sublimation to obtain a high purity polymer-grade monomer without a need for intermediate purification steps such as crystallization, hydrogenation, etc.

Example 2

Purification of FDCA without a Post Oxidation Step

Step 2.1—Oxidation of HMF to FDCA

Oxidation of HMF to FDCA experiment was carried out in a 1 L titanium reactor (Autoclave Engineers, Serial #85-00534-1). The reactor was charged with 440 mL of acetic acid, 23 mL of water, 6.2511 g of cobalt(II) acetate tetrahydrate, 0.44 g of manganese(II) acetate tetrahydrate, and 698 µL of hydrobromic acid (48%). The unit was pressurized to 450 psig using air, and heated to a reaction temperature of 180° C. Air was then sparged in through a dip tube which had eight 229 µm diameter holes at a rate of 4.5 slpm when reactor temperature reached 170° C. Nitrogen was fed to the inlet of the condenser at 4.5 slpm. When desired temperature was achieved, the HMF feed was pumped into the reactor at a rate of 3.6 mL/min through another dip tube which was positioned by the reactor impeller. The composition of the HMF feed for this run was 4.48 wt % HMF, 5.18 wt % AcMF, 0.15 wt % HMF dimer and 5.4 wt. % humins. This addition was performed over a 45 min period. After the addition was complete, the reactor was cooled to room temperature and depressurized. The FDCA solids were then vacuum filtered and dried in a vacuum oven at 75° C. and 200 to 300 torr to give 13.1 g of crude FDCA (with a molar FDCA yield of 80.2%). A detailed analysis of this sample is given in Table 3. This sample is referred as sample 2.1.

Step 2.2 Esterification of FDCA to FDME

FDCA sample 2.1 was esterified in a 75 mL mini Parr reactor model 5050 equipped with an IKA RCT Basic hotplate stirrer. 8 g FDCA sample 2.1, 32 g methanol and TFE stir bar were added to the reactor. The reactor was placed in an aluminum block and was kept insulated. The reactor was then purged a minimum of 5 times with nitrogen. At room temperature, 300 psi of $N_2$ was introduced in the reactor head. The reactor was then heated to a temperature of 200° C. and both the temperature and pressure were monitored. After 4 hr, heat was turned off and the reactor was allowed to cool to room temperature. The pressure was then released and the reactor was opened. The reactor contents (containing mainly FDME product) were removed and transferred to an aluminum pan. Solids were dried overnight on aluminum pan (while methanol was evaporated). The dried solids were then analyzed using HPLC and SEC. This sample of the crude methyl ester of FDCA was referred as Sample 2.2 in Table 3. A portion of the crude methyl ester Sample 2.2 was sublimed using the procedure given above. The sublimed top and bottom samples are labeled 2.3-1 and 2.3-2 in Table 3.

Table 3: Results Obtained After the Analysis of Solids Collected at the End of Stability Tests

TABLE 3

| Sample | L* | b* | Wt. % FDME | Wt. % FDMME | Wt. % FDCA | Wt. % FFME | Humins (ppm) |
|---|---|---|---|---|---|---|---|
| 2.1 (after oxidation) | 90.46 | 25.47 | 0.00 | 0.00 | 98.79 | 0 | 41 |
| 2.2 (after esterification | 91.12 | 25.69 | 82.85 | 15.73 | 0.64 | 0.51 | 455 |
| 2.3-1 (after sublimation, collected from top) | 98.38 | 2.77 | 96.85 | 0.76 | 0 | 2.39 | <10 |
| 2.3-2 (after sublimation, collected from bottom) | 87.93 | 39.77 | 81.74 | 16.75 | 1.51 | 0.37 | 52 |

From the results shown in Table 3, it is unexpectedly found that impure FDCA solids (containing humins & other impurities) can be converted into FDME which can be further purified with sublimation. The purified FDME obtained at the end of sublimation does not contain any humins and also has L*>98 and b*<3. The FDCA solids obtained at the end of oxidation reaction contained some FFCA (1.21 wt %) impurity. This impurity was converted to FFME during the esterification step. In the example 2, the FFME impurity was also removed during the sublimation of the FDME and this resulted in imparting some color to the FDME solids.

What is claimed is:

1. A process, comprising:
   i) oxidizing a feedstock comprising hydroxymethyl furfural and humins in a solvent to produce a mixture comprising crude humins-containing 2,5-furan dicarboxylic acid; and
   ii) filtering the mixture under a high temperature of from 50° C. to 275° C. to obtain a filtrate comprising 2,5-furan dicarboxylic acid having a content of 100 ppm or less of humins, wherein the 2,5-furan dicarboxylic acid is soluble in the solvent during the filtering.

2. The process of claim 1, wherein the high temperature of the filtering step ii) is in the range of from 50° C. to 200° C.

3. The process of claim 1, further comprising a step iii) crystallizing the 2,5-furan dicarboxylic acid having a content of 100 ppm or less of humins to obtain further purified 2,5-furan dicarboxylic acid.

4. The process of claim 1, wherein the solvent is acetic acid or a mixture of acetic acid and water.

\* \* \* \* \*